United States Patent
Abdel-Rahman

(10) Patent No.: US 11,976,023 B1
(45) Date of Patent: *May 7, 2024

(54) SYNTHETIC ROUTE TO 2,2',6,6'-TETRAISOPROPYL-4,4'-DIIODO-AZOBENZENE VIA HOMO-OXIDATIVE CROSS-COUPLING OF ARYL DIAZONIUM SALT USING CU-CATALYZED SANDMEYER-STYLE REACTION

(71) Applicant: KING FAISAL UNIVERSITY, Al-Ahsa (SA)

(72) Inventor: Obadah Subhi Abdel-Rahman, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/543,691

(22) Filed: Dec. 18, 2023

(51) Int. Cl.
*C07C 245/08* (2006.01)
*B01D 15/42* (2006.01)
*B01J 27/055* (2006.01)

(52) U.S. Cl.
CPC .......... *C07C 245/08* (2013.01); *B01D 15/426* (2013.01); *B01J 27/055* (2013.01)

(58) Field of Classification Search
CPC .................................................... C07C 245/08
See application file for complete search history.

(56) References Cited

U.S. PATENT DOCUMENTS 9,827,088 B2    11/2017    Risser et al.
2014/0211293 A1    7/2014    Leguijt et al.

FOREIGN PATENT DOCUMENTS

CN    105367442 A    3/2016
KR    101713303 B1    3/2017

OTHER PUBLICATIONS

Wang et al., Chinese Journal of Chemistry (2022), 40(3), 311-316. (Year: 2022).*

Abboud et al., "Novel family of periodic mesoporous organosilicas containing azobenzene within the pore walls", Microporous and Mesoporous Materials, 249 (2017), pp. 157-164, First available online on Sep. 2017.

Akhtar et al., "Recent trends in the chemistry of Sandmeyer reaction: a review", Mol Divers, Jun. 2022;26(3), pp. 1837-1873, First available online on Aug. 20, 2021.

Koehl et al., "Synthesis of functionalized azobiphenyls and azoterphenyls with improved solubilities for switching applications", Synthesis (2014), 46(17), First available online on May 22, 2014, Abstract Only.

\* cited by examiner

*Primary Examiner* — Laura L Stockton
(74) *Attorney, Agent, or Firm* — Nath, Goldberg & Meyer; Richard C. Litman

(57) ABSTRACT

A new synthetic route to 2,2',6,6'-tetraisopropyl-4,4'-diiodoazobenzene.

13 Claims, No Drawings

SYNTHETIC ROUTE TO 2,2',6,6'-TETRAISOPROPYL-4,4'-DIIODO-AZOBENZENE VIA HOMO-OXIDATIVE CROSS-COUPLING OF ARYL DIAZONIUM SALT USING CU-CATALYZED SANDMEYER-STYLE REACTION

BACKGROUND

1. Field

The present disclosure relates to a new synthetic route to 2,2',6,6'-tetraisopropyl-4,4'-diiodoazobenzene.

2. Description of the Related Art

Azoarylene (also known as diazene or diimide) derivatives are reversible photo switchable chemical compounds composed of two aryl rings linked by a N=N double bond which can change their structural geometry and chemical properties upon irradiation with electromagnetic radiation. Those reversible photoswitchable compounds have been intensively investigated and attracted enormous interests to clarify the mechanism of cis-/trans-isomerization and to understand their applications utilizing alteration of the chemical structures in terms of photoswitching and high-density information optical storage devices.

Azoarylenes are highly accessible through a straightforward step of classical homo-oxidative cross-coupling of aryl diazonium salts using Cu-catalyzed Sandmeyer-style reaction. The product of orange chromophores usually show remarkable a strong $\pi \rightarrow \pi^*$ transition in the visible (Vis) regime of the electromagnetic radiation which can be predictively tuned by introducing substituents on the aryl rings.

SUMMARY

The present subject matter relates to the synthesis of a 2,2',6,6'-tetraisopropyl-4,4'-diiodoazobenzene compound using homo-oxidative cross-coupling of aryl diazonium salt using Cu-catalyzed Sandmeyer-style reaction. This process could be used further for most of organic syntheses of various cross coupling processes including C—C cross coupling Suzuki-Miyaura, Buchwald-Hartwig and Sonogashira reactions.

In one more embodiment, the present subject matter relates to a method of making 2,2',6,6'-tetraisopropyl-4,4'-diiodoazobenzene, the method comprising: suspending 4-iodo-2,6-diisopropylaniline in HC and water to obtain a reaction mixture; maintaining the reaction mixture at 0° C.; adding a solution of $NaNO_2$ and water to the reaction mixture; stirring the reaction mixture; transferring the reaction mixture to a solution of $CuSO_4 \cdot 5H_2O$, $NH_4OH$, $NH_2OH$ and NaOH in water; continuing to stir the reaction mixture; heating the reaction mixture; cooling the reaction mixture and acidifying the reaction mixture to obtain a crude residue; dissolving the crude reaction mixture in distilled water to obtain an organic layer; extracting the organic layer with $CH_2Cl_2$; drying the organic layer to obtain a precipitate; evaporating the $CH_2Cl_2$ and purifying the precipitate; and obtaining the 2,2',6,6'-tetraisopropyl-4,4'-diiodoazobenzene.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the synthesis of 2,2',6,6'-tetraisopropyl-4,4'-diiodoazobenzene compound using homo-oxidative cross-coupling of aryl diazonium salt using Cu-catalyzed Sandmeyer-style reaction. This process could be used further for most of organic syntheses of various cross coupling processes including C—C cross coupling Suzuki-Miyaura, Buchwald-Hartwig and Sonogashira reactions.

The method for synthesizing the 2,2',6,6'-tetraisopropyl-4,4'-diiodoazobenzene comprises: suspending 4-iodo-2,6-diisopropylaniline in HCl and water to obtain a reaction mixture; maintaining the reaction mixture at 0° C.; adding a solution of $NaNO_2$ and water to the reaction mixture; stirring the reaction mixture; transferring the reaction mixture to a solution of $CuSO_4 \cdot 5H_2O$, $NH_4OH$, $NH_2OH$, and NaOH in water; continuing to stir the reaction mixture; heating the reaction mixture; cooling the reaction mixture and acidifying the reaction mixture to obtain a crude residue; dissolving the crude reaction mixture in distilled water to obtain an organic layer; extracting the organic layer with $CH_2Cl_2$; drying the organic layer to obtain a precipitate; evaporating the $CH_2Cl_2$ and purifying the precipitate; and obtaining the 2,2',6,6'-tetraisopropyl-4,4'-diiodoazobenzene according to Scheme 1.

In another embodiment of the present production methods, the reaction mixture may be stirred for about 1 hour.

In a further embodiment of the present production methods, the reaction mixture may be transferred to a solution of $CuSO_4 \cdot 5H_2O$, $NH_4OH$, $NH_2OH$, and NaOH by cannula.

In an embodiment of the present production methods, the reaction mixture may be continually stirred done at 25° C.

In an additional embodiment of the present production methods, the reaction mixture may be heated to 70° C. for at least about 1 hour.

In another embodiment of the present production methods, the reaction mixture may be cooled down before acidifying.

In yet another embodiment of the present production methods, the reaction mixture may be acidified using HCl.

In still another embodiment of the present production methods, the organic layer may be extracted three times using $CH_2Cl_2$.

In a further embodiment of the present production methods, the organic layer may be dried over $MgSO_4$.

In an additional embodiment of the present production methods, the precipitate may be purified using column chromatography.

In a further embodiment of the present production methods, the precipitate may be purified using a petroleum ether and dichloromethane mixture as an eluent. The petroleum ether and dichloromethane mixture may be in a 5:1 ratio.

In another embodiment of the present production methods, the 2,2',6,6'-tetraisopropyl-4,4'-diiodoazobenzene may be an orange crystalline solid.

The following examples relate to various methods of manufacturing the specific compounds and application of the same, as described herein. All compound numbers expressed herein are with reference to the synthetic pathway figures shown above.

EXAMPLES

Example 1

Synthesis of 2,2',6,6'-tetraisopropyl-4,4'-diiodoazobenzene

4-Iodo-2,6-Diisopropylaniline (0.07 mmol) was suspended in 20 mL HCl and 50 mL water. At 0° C. the amine group was diazotized by slowly adding a solution of $NaNO_2$ (5.8 g, 0.08 mol, 1.2 eq.) in 25 mL water. After stirring the mixture at 0° C. for 1 hr, the solution was carefully transferred via a cannula into a freshly prepared solution of $CuSO_4 \cdot 5H_2O$ (34.7 g, 0.14 mol, 2.0 eq.), $NH_4OH$ (75 mL, 0.48 mmol, 6.9 eq.), $NH_2OH$ (10.3 g, 0.15 mmol, 2.1 eq.) and 5 g of NaOH in 50 mL water. Then stirring was continued at 25° C., and the reaction mixture was heated up to 70° C. for 1 hour. The resulting mixture was cooled down and acidified with 25 mL HCl (37%). The crude residue was taken up in a mixture of $CH_2Cl_2$ and distilled water and the organic layer was extracted three times with $CH_2Cl_2$. The combined organic layers were dried over $MgSO_4$ and the solvent was evaporated in vacuo. Purification by column chromatography (eluent: petroleum ether/dichloromethane, 5:1) gave the desired 2,2',6,6'-tetraisopropyl-4,4'-diiodoazobenzene as an orange crystalline solid. Characterization of the prepared compound was determined using $^1$H-NMR (400 MHz, $CD_2Cl_2$): δ 7.09 (s, 4H, $H_{(1)}$), 2.97 (hept, 4H, $_3J$=6.7 Hz, $CH(CH_3)_2$), 1.12 (d, 24H, $_3J$=6.7 Hz, $(CH_3)_2CH$) ppm.

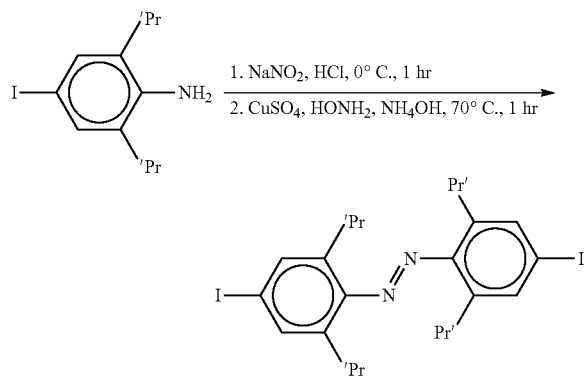

Scheme 1

It is to be understood that the 2,2',6,6'-tetraisopropyl-4,4'-diiodoazobenzene and compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of making 2,2',6,6'-tetraisopropyl-4,4'-diiodoazobenzene, the method comprising:
    suspending 4-iodo-2,6-diisopropylaniline in HCl and water to obtain a reaction mixture;
    maintaining the reaction mixture at 0° C.;
    adding a solution of $NaNO_2$ and water to the reaction mixture;
    stirring the reaction mixture;
    transferring the reaction mixture to a solution of $CuSO_4 \cdot 5H_2O$, $NH_4OH$, $NH_2OH$, and NaOH in water;
    continuing to stir the reaction mixture;
    heating the reaction mixture;
    cooling the reaction mixture and acidifying the reaction mixture to obtain a crude residue;
    dissolving the crude reaction mixture in distilled water to obtain an organic layer;
    extracting the organic layer with $CH_2Cl_2$;
    drying the organic layer to obtain a precipitate;
    evaporating the $CH_2Cl_2$ and purifying the precipitate; and
    obtaining the 2,2',6,6'-tetraisopropyl-4,4'-diiodoazobenzene.

2. The method of making the 2,2',6,6'-tetraisopropyl-4,4'-diiodoazobenzene of claim 1, wherein the reaction mixture is stirred for about 1 hour.

3. The method of making the 2,2',6,6'-tetraisopropyl-4,4'-diiodoazobenzene of claim 1, wherein the reaction mixture is transferred to a solution of $CuSO_4 \cdot H_2O$, $NH_4OH$, $NH_2OH$, and NaOH by cannula.

4. The method of making the 2,2',6,6'-tetraisopropyl-4,4'-diiodoazobenzene of claim 1, wherein the continuing to stir the reaction mixture is conducted at about 25° C.

5. The method of making the 2,2',6,6'-tetraisopropyl-4,4'-diiodoazobenzene of claim 1, wherein the reaction mixture is heated to about 70° C. for at least about 1 hour.

6. The method of making the 2,2',6,6'-tetraisopropyl-4,4'-diiodoazobenzene of claim 1, wherein the reaction mixture is cooled down before acidifying.

7. The method of making the 2,2',6,6'-tetraisopropyl-4,4'-diiodoazobenzene of claim 1, wherein the reaction mixture is acidified using HCl.

8. The method of making the 2,2',6,6'-tetraisopropyl-4,4'-diiodoazobenzene of claim 1, wherein the organic layer is extracted three times using $CH_2Cl_2$.

9. The method of making the 2,2',6,6'-tetraisopropyl-4,4'-diiodoazobenzene of claim 1, wherein the organic layer is dried over $MgSO_4$.

10. The method of making the 2,2',6,6'-tetraisopropyl-4,4'-diiodoazobenzene of claim 1, wherein the precipitate is purified using column chromatography.

11. The method of making the 2,2',6,6'-tetraisopropyl-4,4'-diiodoazobenzene of claim 10, wherein the precipitate is purified using a petroleum ether and dichloromethane mixture as an eluent.

12. The method of making the 2,2',6,6'-tetraisopropyl-4,4'-diiodoazobenzene of claim 11, wherein the petroleum ether and dichloromethane mixture is in a 5:1 ratio.

13. The method of making the 2,2',6,6'-tetraisopropyl-4,4'-diiodoazobenzene of claim 10, wherein the 2,2',6,6'-tetraisopropyl-4,4'-diiodoazobenzene is an orange crystalline solid.

* * * * *